United States Patent [19]

Block

[11] 4,080,385
[45] Mar. 21, 1978

[54] PREPARATION OF ALKOXY PHOSPHOLANE OXIDES AND SULPHIDES

[75] Inventor: Hans-Dieter Block, Cologne, Germany

[73] Assignee: Bayer Aktiengesellschaft, Leverkusen, Germany

[21] Appl. No.: 741,577

[22] Filed: Nov. 12, 1976

[30] Foreign Application Priority Data

Nov. 21, 1975 Germany .............................. 2552319

[51] Int. Cl.$^2$ .............................................. C07F 9/53
[52] U.S. Cl. .............................. 260/606.5 P; 260/936
[58] Field of Search .......................... 260/606.5 P, 936

[56] References Cited

U.S. PATENT DOCUMENTS

| | | | |
|---|---|---|---|
| 2,663,737 | 12/1953 | McCormack | 260/606.5 P |
| 2,663,738 | 12/1953 | McCormack | 260/606.5 P |
| 2,663,739 | 12/1953 | McCormack | 260/606.5 P |
| 2,853,473 | 9/1958 | Campbell et al. | 260/606.5 P X |
| 3,331,878 | 7/1967 | Priestley | 260/606.5 P |
| 4,010,209 | 3/1977 | Smith et al. | 260/606.5 P |

OTHER PUBLICATIONS

Chemical Abstracts, 73, 25650g (1970).
Chemical Abstracts, 79, 146596b (1973).
Chemical Abstracts, 69, 2985y (1968).
Tomioda, Tetrahedron Letters, 50 5059 (1973).
Chemical Abstracts, 62, 6505e (1965).
Chemical Abstracts, 72, 44501e (1970).

*Primary Examiner*—Helen M. S. Sneed
*Attorney, Agent, or Firm*—Burgess, Dinklage & Sprung

[57] ABSTRACT

A process for the production of an alkoxy phospholane oxide or sulphide of the formula

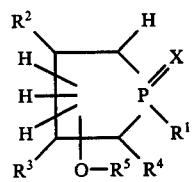

in which $R^1$ is an alkyl, alkoxy or aryl radical having up to 14 carbon atoms.

$R^2$, $R^3$ and $R^4$ each independently is a $C_1$ to $C_4$ alkyl radical, hydrogen, chlorine or bromine, $R^5$ is an alkyl, alkenyl, alkynyl radical having from 1 to 14 carbon atoms, and X is oxygen or sulphur, comprising reacting a phospholene oxide or sulphide of the formula

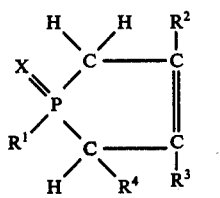

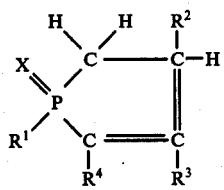

or

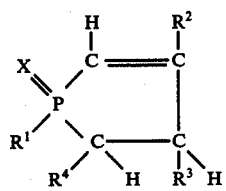

with an alcohol of the formula

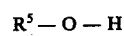

in the presence of an alkaline catalyst, such as sodium methylate. The products catalyze the conversion of isocyanates into carbodiimides with evolution of carbon dioxide.

5 Claims, No Drawings

PREPARATION OF ALKOXY PHOSPHOLANE OXIDES AND SULPHIDES

This invention relates to a new process for the production of alkoxy phospholane oxides and sulphides.

Five-membered cyclic phosphine oxides and sulphides, i.e. phospholene oxides and phospholane oxides and also the corresponding sulphides, are known to be effective catalysts for the conversion of isocyanates into carbodiimides with evolution of carbon dioxide. They are obtained by reacting alkyl or aryl dihalogen phosphines with 1,3-dienes, and hydrolyzing or sulphydrolyzing the dihalogen phospholene obtained as a primary product, optionally followed by hydrogen (cf, for example U.S. Pat. Nos. 2,663,737, 2,663,738). Unfortunately, the range of dienes which may readily be obtained on a commercial scale is limited to butadiene, isoprene, dimethyl butadiene and chloroprene. Similarly, only a few monosubstituted dihalogen phosphines may readily be obtained on a commercial scale. Accordingly, only a few phospholene and phospholane oxides have hitherto been considered for commercial application. For this reason, it has been difficult in the past to provide carbodiimide-forming catalysts optimally adapted to the numerous isocyanates used on a commercial scale, their solutions and mixtures. One solution to this problem is to modify phospholene oxides and phospholane oxides, and also the corresponding sulphides, with alkyl radicals.

In addition, the incorporation of alkyl groups, for example in the form of alkoxy groups, represents a possible means of producing phospholane oxides substituted by functional groups which may subsequently be incorporated into macromolecules, for example through covalent bonds. Alkoxy phospholane oxides are known per se. They are obtained by the light-induced addition of alcohols to 1-alkyl-2-phospholenes, followed by oxidation of the alkoxy phospholanes formed with percarboxylic acids to form the 1-substituted 3-alkoxy phospholane oxides.

However, 3-phospholenes do not undergo an addition reaction with any alcohol under these conditions. In addition, the reaction can only be applied to primary alcohols because secondary alcohols, for example, give rise to side reactions (H. Tomioda, Y. Izawa, Tetrah. Letters 50, 5059 (1973)).

Accordingly, the object of the present invention is to provide a simple process for producing alkoxy phospholane oxides and sulphides from phospholene oxides and sulphides. More particularly, the object of the invention is to enable the reaction to be carried out both the primary and also with secondary and tertiary alkoxy groups.

The present invention relates to a process for the production of alkoxy phospholane oxides and sulphides corresponding to the general formula (I):

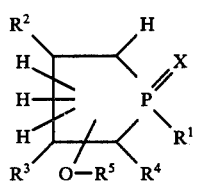

in which $R^1$ represents an alkyl radical, an alkoxy radical or an aryl radical having up to 14 carbon atoms, $R^2$, $R^3$, $R^4$ independently of one another represent a $C_1$ to $C_4$ alkyl radical, hydrogen, chlorine or bromine, $R^5$ represents an alkyl, alkenyl, alkynyl radical having from 1 to 14 carbon atoms, and X represents oxygen or sulphur, distinguished by the fact that phospholene oxides or sulphides corresponding to the general formula (II), (IIIa) or (IIIb):

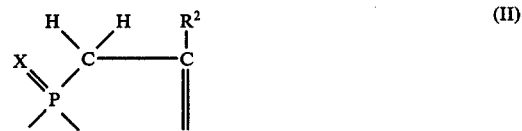

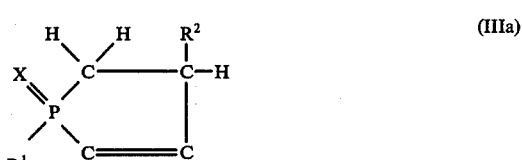

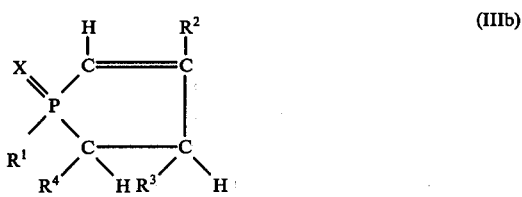

in which $R^1$, $R^2$, $R^3$, $R^4$ and X have the same meaning as in formula (I), are reacted with alcohols corresponding to the general formula (IV):

in the presence of alkaline catalysts.

$R^1$ may be unsaturated and, when aryl, it may also carry alkyl substituents, e.g. cloro, bromo, methyl, ethyl, and the like.

Preferably, $R^1$ represents methyl, ethyl, propyl or phenyl, $R^2$, $R^3$ and $R^4$ represent methyl or hydrogen and $R^5$ represents methyl, ethyl, allyl or propyl.

The starting materials of formulae (II) and (III) for the process according to the invention are known or may be obtained by known methods (cf. G. M. Kosolapoff, L. Maier, Organic Phosphorus Compounds, Wiley-Interscience, New York, 1972 et. seq., Vol. 3, pp 370-371, pp 458-463 and Vol. 4, pp 9-10, page 48).

The following are examples of these 5-membered unsaturated phosphine oxides of which the double bond may be situated either in the 2,3 or in the 3,4- position:

1-methyl-1-oxophospholene
1-ethyl-1-oxophospholene 1-butyl-1-oxophospholene
1-(2-ethylhexyl)-1-oxophospholene
1-methyl-1-thiophospholene
1-(2-chlorethyl)-1-oxophospholene
1-phenyl-1-oxophospholene
1-p-tolyl-1-oxophospholene 1-chloromethyl-1-oxophospholene
1,3-dimethyl-1-oxophospholene
1,3-dimethyl-1-thiophospholene
1,2-dimethyl-1-oxophospholene
1-methyl-3-chloro-1-oxophospholene
1-methyl-3-bromo-1-oxophospholene
1-chlorophenyl-1-oxophospholene
1,3,4-trimethyl-1-oxophospholene
1,2,4-trimethyl-1-oxophospholene
1,2,2-trimethyl-1-oxophospholene
1-phenyl-1-thiophospholene
1-phenyl-3-methyl-1-oxophospholene
1-phenyl-2,3-di-methyl-1-oxophospholene
1-methoxy-1-oxophospholene
1-ethoxy-1-oxophospholene
1-dodecyloxy-1-oxophospholene Alcohols of general formula (IV) suitable for use in the process according to the invention are both primary and also secondary and tertiary alcohols. In addition, the hydrocarbon radical $R^5$ may contain substituents which do not react with the alkaline catalyst or react so slowly that they do not interfere with the required reaction, e.g. phenyl, lower alkoxy, phenoxy, halophenoxy, hydroxy, hydroxy lower alkoxy, hydroxy lower alkoxy lower alkoxy, lower alkyl mercapto, amino, carboxy, carbo-lower alkoxy, lower alkyl, and the like.

The following are examples of alcohols which may be used in accordance with the invention:

Methanol, ethanol, n-propanol, i-propanol, n-butanol, i-butanol, sec.-butanol, tert.-butanol, the isomeric pentanols, hexanols, heptanols, octanols, nonanols, decanols, dodecanols, also cyclopentanol, cyclohexanol, benzyl alcohol, 2-phenyl ethanol, 2-methoxy ethanol, 2-phenoxy ethanol, 2-pentachlorophenoxy ethanol, allyl alcohol, methallyl alcohol, glycol, diethylene glycol, triethylene glycol, propylene glycol, trimethylol propane, glycerol, 1,3-propane diol, 2-methylmercapto ethanol, 1,4-butene diol, 1,4-butine diol and propargyl alcohol.

Thioalcohols and thiophenols are also similarly added to phosphine oxides and sulphides to form the alkyl and aryl mercapto phospholane oxides and sulphides. Suitable thioalcohols and thiophenols are, for example, methyl mercaptan, ethyl mercaptan, n-butyl mercaptan, i-propylmercaptan, dodecyl mercaptan, tert. dodecyl mercaptan, the sodium salt of thioglycolic acid, thioglycolic acid ethyl ester, thiophenol and thiocresol.

It is also possible to use mixtures of alcohols.

Basic catalysts suitable for use in the process according to the invention are the soluble metal alcoholates corresponding to the particular alcohol used, in particular the sodium and potassium salts, alkali metal and alkaline earth metal hydroxides and their aqueous solutions, also all those agents which are known to be able to convert the particular alcohols used into their metal salts. The last of these groups includes, for example, elemental alkali metals, alkaline earth metals, earth metals, Grignard compounds and organic alkali metal compounds.

The reaction products of general formula (I) are generally mixtures of compounds corresponding to the formulae:

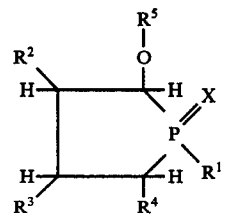

(Ia)

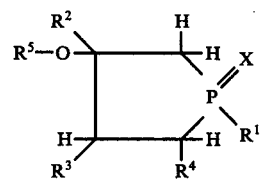

(Ib)

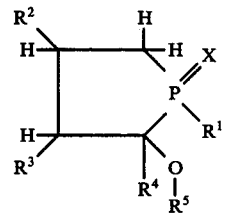

(Ic)

Investigations have shown that the structure (Ib) is generally the predominant component.

The process according to the invention is generally carried out by heating the requisite quantities of the reactants of general formula (II) or (III) and (IV), together with the alkaline catalyst, to the reaction temperature and leaving the reaction mixture at that temperature for a certain period. However, the object of the reaction is also achieved by initially introducing one of the reactants or the alkaline catalyst or any combinations thereof and subsequently adding the missing constituents of the reaction mixture.

The phospholene oxides or sulphides of general formulae (II) or (III) required for the reaction and the alcohols of general formula (IV) are generally used in molar ratios of from 5:1 to 1:50, preferably 1:1 to 1:5. The quantity of alkaline catalyst to be added amounts to between about 0.5 and approximately 100 mole %, based on whichever reactant of formulae (II), (III) or (IV) is present in lesser molar amount.

The reaction may be carried out in a solvent which does not react with the reactants under the conditions applied, although it is preferred not to use a solvent.

The reaction temperatures are in the range of about 30° C to about 200° C, temperatures in the range of about 60° C to 150° C being preferred. The reaction is carried out preferably at normal pressure, although it may also be carried out at a superatmospheric pressure or subatmospheric pressure. Working at pressures such as these affords an advantage in cases where, as a result of applying these pressures, a temperature which would otherwise be difficult if not impossible to adjust is reached in the reaction mixture.

The atmosphere over the reaction mixture should be kept substantially free from acid gases because acid gases reduce the activity of the catalyst.

The reaction time is between about 0.3 and 60 hours, being governed by the concentration and type of alkaline catalyst used, by the reaction temperature and by the required conversion.

The reaction product may be isolated from the reaction mixture in the usual way. Readily volatile unreacted starting materials and/or solvents are most easily separated off by distillation. The alkoxy phospholane oxides or sulphides may be further separated off and/or purified not only by distillation, preferably in vacuo, but also by extraction with a suitable solvent selected, for example, from chlorinated hydrocarbons, aromatic hydrocarbons, esters, alcohols, ketones, nitriles, etc., optionally after the addition of another auxiliary solvent such as, for example, water for improving the purification effect. If desired, the alkaline catalyst may be destroyed by neutralization before working up.

The alkoxy phospholane oxides and sulphides obtained by the process according to the invention are highly active catalysts for carbodiimide-forming reactions. They may be successfully used for the production of monomeric carbodiimides from monoisocyanates, long-chain alkoxy radicals facilitating separation of the catalyst from the carbodiimide produced. They are equally suitable for the production of polycarbodiimide foams from diisocyanates and polyisocyanates.

The process according to the invention is illustrated by the following Examples:

EXAMPLE 1

A solution of 232 g of 1-methyl-1-oxophospholene isomer mixture and 22.5 g of sodium methylate in 390 ml of methanol is heated under reflux for 16 hours. Methanol is then distilled off, and the residue is taken away in 200 ml of water, saturated with sodium chloride and extracted five times with the same volume of chloroform. The solvent is distilled off from the combined chloroform extracts and the remaining liquid is separated by means of a column into 14 g of 1-methyl-1-oxo-phospholine ($bp_{0.5}$ 69–81° C) and 258 g of 1-methyl-1-oxo-(2,3)-methoxy phospholane ($bp_{0.5}$ 92–102° C). Conversion of the 1-methyl-1-oxophospholine: 92%.

EXAMPLES 2 2–5

The quantity of catalyst indicated in the first column of the following Table is added to solutions of 232 g of 1-methyl-1-oxophospholene in 390 ml of methanol, followed by boiling (at about 70° C) for the period indicated in the second column. Thereafter, methanol is distilled off, and the residue is taken up in 300 ml of water, saturated with sodium chloride and extracted five times with the same volume of chloroform. The solvent is distilled off from the combined chloroform extracts. The ratio of 1-methyl-1-oxophospholene to 1-methyl-1-oxo(2,3)-methoxy phospholane in the residue is determined by gas chromatography and the conversion of the 1-methyl-1-oxophospholene used into 1-methyl-1-oxo-(2,3)-methoxy phospholane is calculated therefrom.

| Quantity of catalyst | Reaction time | Conversion |
|---|---|---|
| 2.4 g of NaOCH₃ | 16 hours | 26% |
| 108 g of NaOCH₃ | 2 hours | 37% |
| 108 g of NaOCH₃ | 8 hours | 93% |
| 16 g of NaOH, 16 g H₂O | 8 hours | 87% |
| 16 g of NaOH | 16 hours | 78% |

EXAMPLE 6

A solution of 348 g of 1-methyl-1-oxophospholene in 600 ml of allyl alcohol, of which part has been converted into sodium allyl alcoholate by reaction with 7 g of sodium, is heated for 16 hours at 98° C. Thereafter, the conversion of the 1-methyl-1-oxophospholene into 1-methyl-1-oxo-(2,3)-allyloxyphospholane, as determined by gas chromatography, amounts to 76%. For working up, the allyl alcohol is distilled off at 98–100° C under a pressure decreasing to 20 mm Hg. The residue is taken up in 400 ml of water and neutralized with sulphuric acid. The neutral aqueous solution is extracted five times with the same volume of chloroform. The solvent is initially distilled off with residues of allyl alcohol from the combined chloroform extracts, after which unreacted 1-methyl-1-oxophospholene (29 g $bp_1$ 81°–98° C) is removed therefrom by fractionation in vacuo in a column filled with Raschig rings and, finally, 1-methyl-1-oxo-(2,3)-allyloxy phospholane ($bp_1$ 109°–118° C) is distilled over.

Yield: 407 g (78% of the theoretical amount, based on the 1-methyl-1-oxophospholene used)

EXAMPLES 7–10

Following the same procedure as in tests 1 to 6, the alcohols (300 ml) identified in column 1 of the following Table are reacted for the periods indicated at certain temperatures (3rd column) with 116 g of 1-methyl-1-oxo-phospholine in the presence of the quantity indicated in the second column of an alkali metal alcoholate. The conversion after the particular predetermined reaction time is determined by gas chromatography in the same way as before.

| Alcohol | Catalyst | Reaction time | Conversion |
|---|---|---|---|
| ethanol | 0.18 moles of NaOC₂H₅ | 16 hours/85° C | 85% |
| 2-ethyl hexanol | 0.10 moles of NaOC₈H₁₇ | 8 hours/98° C | 80% |
| i-propanol | 0.10 moles NaOC₃H₇(i) | 8 hours/88° C | 66% |
| t-butanol | 0.05 moles of KOC₄H₉(t) | 8 hours/70° C | 6.5% |

EXAMPLE 11

1 g of sodium is dissolved in a mixtur of 65 g of 1-ethyl-1-oxophospholene and 30 g of methanol. The reaction mixture is heated to boiling point over a period of about 24 hours. Thereafter, vacuum is applied, after which first methanol, then a residue of 1-ethyl-1oxo-phospholene (2 g) and, finally, 66 g of 1-ethyl-1-oxo-(2,3)-methoxy phospholane ($bp_1$ 105°–116° C) are distilled off under decreasing pressure.

EXAMPLE 12

89 g of 1-phenyl-1-oxophospholene, 200 ml of methanol and 6 g sodium methylate are boiled under reflux for 32 hours. After the methanol has been distilled off, the residue is taken up in 300 ml of toluene, washed three times with 30 ml portions of water and thereafter the solution is freed from solvent by distillation. Evacuation for three hours to 1 mm Hg at 120° C leaves 101 g of a residue which, according to ¹H-NMR-analysis, consists of a mixture of 1-phenyl-1-oxo-(2,3)-methoxy phospholane isomers.

EXAMPLE 13

132 g of 1-methyl-1-thiophospholene, 300 ml of methanol and 10.8 g of sodium methylate are heated to boiling point over a period of 8 hours. Thereafter, the conversion of the 1-methyl-1-thiophospholene into 1-methyl-1-thio-(2,3)-methoxy phospholane, as determined by gas chromatography, amounts to 66%. After neutralization with sulphuric acid, evaporation of the methanol, dissoluton in 400 ml of methylene chloride, washing the methylene chloride phase with three 50 ml portions of water and evaporation of the solvent, 141 g of a mixture of 1-methyl-1-thiophospholine and 1-methyl-1-thio-(2,3)-methoxy phospholane are left. The components 1-methyl-1-thiophospholine (25 g) and 1-methyl-1-thio-(2,3)-methoxy phospholane (103 g ≧ 63% of the theoretical, based on the material used) can be isolated therefrom by distillation.

EXAMPLE 14

132 g of 1-methoxy-1-oxophospholene, 300 ml of methanol and 11 g of sodium methylate are heated to 70° C over a period of 16 hours. The reaction mixture is neutralized with carbon dioxide when cold, the methanol is removed in vacuo and the residue is taken up in 100 ml of water and repeatedly reextracted with chloroform. The combined chloroform phases are concentrated by evaporation and the residue left is fractionated into 8 g of 1-methoxy-1-oxophospholene and 139 g of 1-methoxy-1-oxo-(2,3)-methoxyphospholane.

EXAMPLE 15

73 g of 1-ethoxy-1-oxophospholene, 200 ml of ethanol and 6 g of sodium ethylate are heated under reflux to boiling point over a period of 38 hours. Ethanol is then distilled off, the residue is diluted with 50 ml of water, the aqueous phase is neutralized with sulphuric acid and the neutral aqueous phase is extracted 4 times with the same volume of chloroform. 79 g of 1-ethoxy-1-oxo-(2,3)-ethoxy phospholane are obtained from the organic extracts by distillation in vacuo.

EXAMPLE 16

58 g of a mixture of 1-methyl-1-oxo-phospholene isomers and 45 g of n-butyl mercaptan are mixed, followed by the addition of approximately 0.1 g of elemental sodium. The sodium dissolves in the reaction mixture on heating. After 16 hours at 95° to 100° C, the reaction is distilled. After a first fraction of 15.5 g, 72 g of 1-methyl-1-oxo butyl mercapto phospholane (bp$_2$ 156°–160° C) are abtaines, corresponding to a yield of 70% of the theoretical amount.

EXAMPLE 17

350 g of an unsaturated polyester having an acid number 9, produced form equivalent quantities of maleic acid anhydride and tetraethylene glycol are mixed with 150 g 1-methyl-1-oxo-(2,3)-allyloxy-phospholane obtained according to Example 6, subsequently heated slowly to 150° C with 7.5 g benzoyl peroxide under agitation and then agitated for ½ hour. The crumbly product produced is extracted for 2 days with toluene and 2 days with chloroform. P-content = 2,4 %.

EXAMPLE 18

168 g 1,6-hexamethylenediisacyanate are heated to 150° C with 5 g of a catalyst according to Example 17. After the formation of 14 liters carbon dioxide, the product is filtered and formed into thin layers. Then it has a viscosity $\eta_{24}=580$ liters cP and an isocyanate content of 23%.

When applied to a glass plate, the product forms a scratch-resistant elastic film as a result of the reaction with atmospheric moisture.

EXAMPLE 19

A mixture of 111 parts by weight 1-isocyanato-3,3,5-trimethyl-5-isocyanatomethyl-cyclohexane and 84 parts by weight 1,6-hexamethylene diisocyanate is heated to 160° C and mixed with 5 g of a catalyst according to Example 17. After the development of 7.3 litres carbon dioxide, the product (viscosity $\eta_{24}=170$ cP) is fltered and formed into thin layers at 80° C/0.12 Torr, with monomeric isocyanate being drawn off. The product formed into thin layers has, in addition to carbodiimides a high content of isocyanatoureton imines. ($\eta_{24}=916$ cP; isocyanate content = 23.9).

EXAMPLE 20

A mixture of 17 g of 1-methyl-1-oxo-(2,3)-methoxyphospholane, described in Example 1 and 1 g of a polysiloxane-polyalkylene glycol (as foam stabiliser) and 8 g of glycerine was prepared in a paper beaker. 200 g of crude diphenylmethane diisocyanate having a viscosity of 195 cP/25° C and an isocyanate content of 31.1% which had been prepared by anilineformaldehyde condensation followed by phosgenation were added to this mixture with vigorous stirring. The reaction mixture was poured into a paper mould.

| Reaction times | $t_R$ = 15 sec | $t_R$ = stirring time |
|---|---|---|
| | $t_L$ = 20 sec | $t_L$ = resting time |
| | $t_A$ = 80 sec | $t_A$ = setting time |
| | $t_S$ = 150 sec | $t_S$ = rising time |
| | $t_K$ = 180 sec | $t_K$ = time required for product to become free from tackiness. |

The resting time is the time during which the reaction mixture remains optically unchanged.

The setting time is the time required for the reaction to progress to the stage where threads can be drawn from the mixture.

The rising time is the time up to which the reaction mixture rises when left to foam up without restriction.

The time required for the product to become free from tackiness is the time after which articles which come into contact with the foam no longer adhere to its surface.

The foam obtained had the following physical properties:

| Density | 15 kg/m$^3$ | DIN 53420 |
|---|---|---|
| Compressive Strength | 0,6 kp/cm$^2$ | DIN 53421 |
| Resistance to bending in the heat | 130° C | DIN 53424 |
| Coefficient of thermal conductivity | 0,032 kcal/m/h | DIN 52612 |
| Burning test on small sample (length of burnt sample) | 64/75 K1,F1 | DIN 4102. |

What is claimed is:

1. A process for the production of an alkoxy phospholane oxide or sulphide of the formula

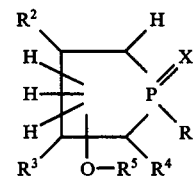

in which

R$^1$ is an alkyl, alkoxy or aryl radical having up to 14 carbon atoms, $R^2$, $R^3$ and $R^4$ each independently is a $C_1$ to $C_4$ alkyl radical or hydrogen, $R^5$ is an alkyl, alkenyl, or alkynyl radical having from 1 to 14 carbon atoms, and X is oxygen or sulphur, comprising reacting a phospholene oxide or sulphide of the formula

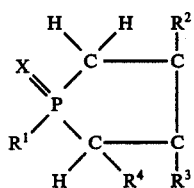

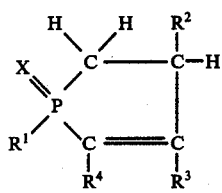

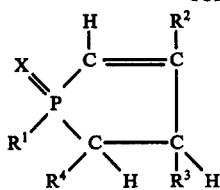

with an alcohol of the formula $R^5$—O—H at a temperature of about 30° to 200° C and in the presence of an alkaline catalyst, the phospholene oxide or sulphide being employed in a molar ratio of about 5 : 1 to 1 : 50 relative to the alcohol and the alkaline catalyst being present in about 0.5 to 100 mole % based on whichever reactant is present in lesser molar amount.

2. A process as claimed in claim 1, wherein a metal alcoholate is used as the catalyst.

3. A process as claimed in claim 2, wherein sodium methylate is used as the catalyst.

4. A process as claimed in claim 1, wherein $R^1$ is methyl, ethyl, propyl or phenyl, $R^2$, $R^3$ and $R^4$ each independently is methyl or hydrogen, and $R^5$ is methyl, ethyl, propyl or allyl.

5. A process as claimed in claim 4, wherein sodium methylate is used as the catalyst.

* * * * *